(12) United States Patent
Flanagan

(10) Patent No.: US 7,709,045 B2
(45) Date of Patent: May 4, 2010

(54) MEDICAL DEVICES COATED WITH POROUS CARBON AND METHODS OF MANUFACTURING THE SAME

(75) Inventor: Aiden Flanagan, Kilcolgan (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 426 days.

(21) Appl. No.: 11/412,877

(22) Filed: Apr. 28, 2006

(65) Prior Publication Data

US 2007/0255393 A1 Nov. 1, 2007

(51) Int. Cl.
- A61L 33/00 (2006.01)
- B05D 3/02 (2006.01)
- A61F 2/06 (2006.01)

(52) U.S. Cl. .............. 427/2.1; 427/2.24; 427/2.25; 427/2.3; 427/2.31; 427/226; 427/228; 427/554; 427/555; 427/586; 623/1.1; 623/1.42; 623/1.43; 623/1.44; 623/1.46

(58) Field of Classification Search .............. 427/2.1, 427/2.24, 586, 532, 554, 555, 2.25, 2.28, 427/2.3, 2.31, 226, 228; 623/1.1, 1.11, 1.42, 623/1.43, 1.44, 1.46
See application file for complete search history.

(56) References Cited

U.S. PATENT DOCUMENTS

| | | | | |
|---|---|---|---|---|
| 5,011,486 A | * | 4/1991 | Aebischer et al. | 623/1.15 |
| 5,273,788 A | * | 12/1993 | Yu | 427/554 |
| 5,769,884 A | * | 6/1998 | Solovay | 623/1.13 |
| 5,820,967 A | | 10/1998 | Gadkaree | |
| 5,833,707 A | * | 11/1998 | McIntyre et al. | 606/198 |
| 6,071,305 A | * | 6/2000 | Brown et al. | 623/1.43 |
| 6,117,618 A | * | 9/2000 | Yedur et al. | 430/296 |
| 6,156,697 A | | 12/2000 | Gadkaree | |
| 6,355,350 B1 | | 3/2002 | Guseva et al. | |
| 6,569,107 B2 | | 5/2003 | Jalisi et al. | |
| 2002/0177891 A1 | * | 11/2002 | Parodi | 623/1.15 |
| 2003/0139735 A1 | * | 7/2003 | Neuberger | 606/3 |
| 2004/0181271 A1 | | 9/2004 | DeSimone | |
| 2005/0079200 A1 | * | 4/2005 | Rathenow et al. | 424/423 |
| 2006/0004356 A1 | * | 1/2006 | Bilski et al. | 606/51 |
| 2006/0111546 A1 | | 5/2006 | Pacetti | |
| 2007/0073281 A1 | * | 3/2007 | Johnson et al. | 606/15 |

OTHER PUBLICATIONS

International Search Report and Written Opinion, PCT/US2007/007700, Jun. 10, 2008.
International Preliminary Report on Patentability and Written Opinion of the International Searching Authority (PCT/US2007/007700), mailed Nov. 6, 2008.

* cited by examiner

*Primary Examiner*—Timothy H Meeks
*Assistant Examiner*—Cachet I Sellman
(74) *Attorney, Agent, or Firm*—Kenyon & Kenyon LLP

(57) ABSTRACT

A method of creating a porous carbon coating on a medical device by applying a precursor carbon material on the medical device and then pyrolysing the precursor carbon material by laser irradiation. The laser irradiation may be focused to carbonize only certain portions of the medical device and any uncarbonized areas can be removed by solvent washing. Also provided is a medical device having a carbonized coating created according to the method of the present invention.

19 Claims, 3 Drawing Sheets

MEDICAL DEVICES COATED WITH POROUS CARBON AND METHODS OF MANUFACTURING THE SAME

TECHNICAL FIELD

The present invention relates to porous carbon coatings on a medical device and methods of manufacturing the same.

BACKGROUND

Many implantable medical devices have a coating in which the coating can perform various functions, such as improving the biocompatibility of the device or serving as a drug delivery system. Also, certain types of porous coatings have been proposed to encourage the migration and normal growth of tissue onto the coating. This feature is beneficial in medical devices because it can enhance its effectiveness and reduce the incidence of unwanted effects and complications such as thrombosis, infection, scarring, or abnormal tissue growth.

One type of porous coating is a porous carbon coating, which has been demonstrated to be highly biocompatible. Porous carbon coatings are able to serve as localized drug delivery systems, which is beneficial in improving the effectiveness of medical devices. Therapeutic agents can be loaded into a porous carbon coating on a medical device and released into the surrounding fluid or tissue after implantation.

There are various methods for creating a porous carbon coating on a medical device, including chemical vapor deposition, physical vapor deposition, and sputtering. Porous carbon can also be created by carbonization in which a carbon-containing precursor material, such as wood, cellulose, coal, or synthetic polymer is pyrolysed. During pyrolysis, the carbon-containing precursor material decomposes, with most of the non-carbon elements, such as hydrogen, nitrogen, and oxygen being removed in tarry or gaseous form. The resulting carbonization of the carbon-containing precursor material transforms it into a solid porous carbon mass.

U.S. Patent Publication No. 2005/0079200 (Rathenow et al.), whose entire disclosure is incorporated by reference herein, describes porous carbon coatings on medical devices created by coating the medical device with a polymer film and then pyrolysing the polymer film by oven heating at high temperatures. The oven heating method of Rathenow results in the uniform carbonization of all parts of the medical device coated with the polymer film.

SUMMARY OF THE INVENTION

The present invention is directed to creating a non-uniform porous carbon coating limited to certain portions of a medical device. In an embodiment, the present invention provides a method of creating a porous carbon coating on a medical device by providing a medical device coated with a precursor carbon material, wherein the medical device has first and second portions. The method further comprises heating the precursor carbon material on at least the first portion of the medical device with a laser to form a carbonized layer. In other embodiments, the precursor material on both the first and the second portions of the medical device are heated with a laser, and wherein the porosity of the carbonized layer in the first portion is different from the porosity of the carbonized layer in the second portion. In these embodiments, the differing porosities are created by the use of additives in the precursor carbon material, by various after-treatments to the carbonized layer, or by laser heating under different sets of heating conditions.

In certain embodiments, certain areas of the medical device may be cooled by the use of streaming gas or fluid, or a cooling element. Any uncarbonized precursor carbon material may be removed by various methods, including solvent washing. The methods of the present invention may further comprise the step of incorporating a therapeutic agent into the carbonized porous carbon layer.

In another embodiment, the present invention provides a medical device having a porous carbon coating on a portion of the medical device, wherein the portion is less than the entire surface of the medical device, and wherein the porous carbon coating carries a therapeutic agent and provides for directionally controlled release of the therapeutic agent. The porous carbon coating may be on the outer diameter, inner diameter, or the side walls of a stent.

DETAILED DESCRIPTION

Definitions: The term "porosity" as used herein refers to the characteristics of the pores, including the size, shape, dimensions, number, density, volume, ratio of the volume of all the pores in a material to the volume of the whole, structure, organization, and architecture of the pores, and whether the pores are closed or open. The term "directionally controlled release" as used herein refers to the ability to release, discharge, or distribute a substance in certain directions or into certain spaces. The term "precursor carbon material" as used herein refers to any carbon-based or carbon-containing material which can become transformed into a solid porous carbon mass upon pyrolysis and/or carbonization.

Figure 1A:
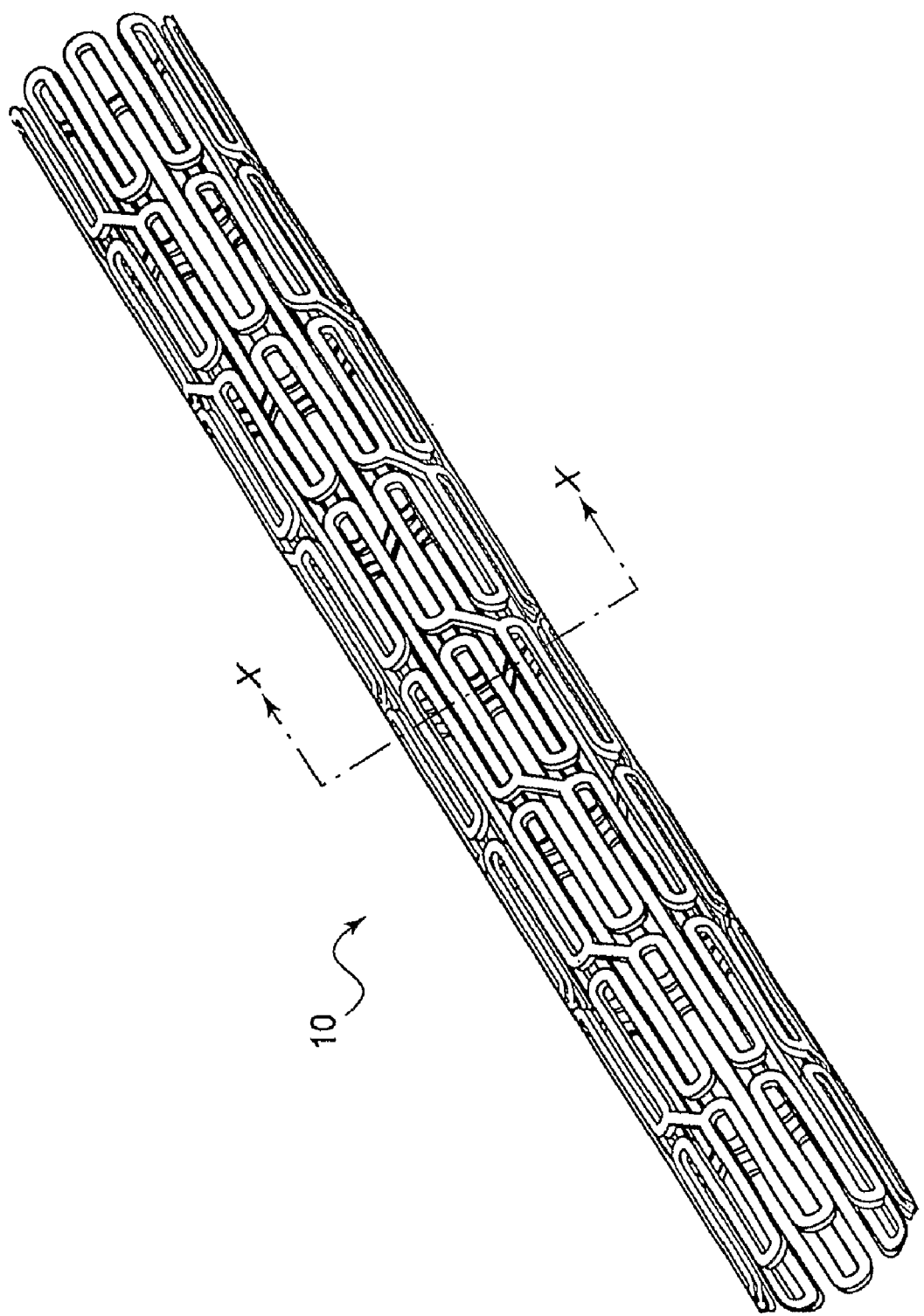
FIG. 1A is a perspective view of a bare, uncoated stent which can be coated according to the methods of the present invention.
Figure 1B:
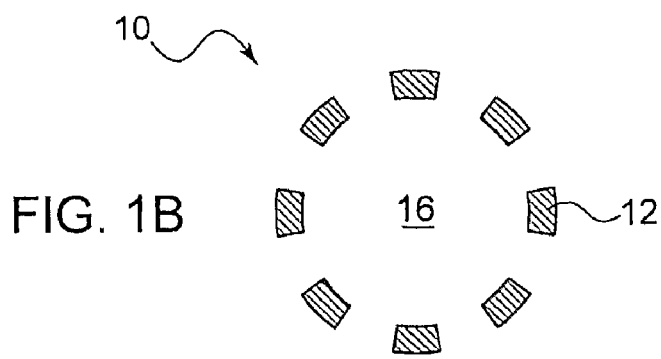
FIG. 1B is a cross-sectional view of the stent of FIG. 1A taken at line X-X.
Figure 2:
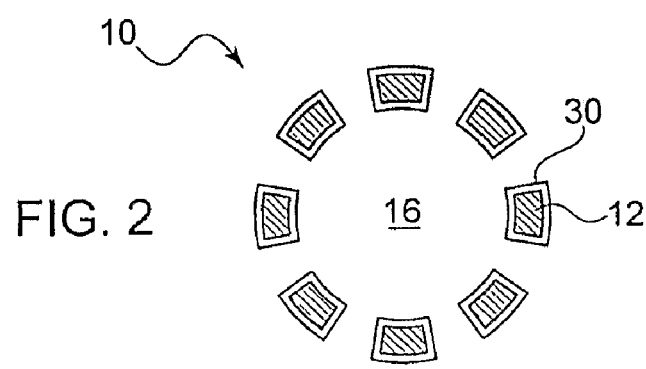
FIG. 2 is a cross-sectional view of the stent of FIG. 1A with a precursor carbon-containing material coated onto the stent.

The present invention provides methods of coating a medical device with a porous carbon coating and a medical device coated by such methods. Referring to FIGS. 1A and 1B, one example of a medical device that can be coated according to the methods of the present invention is a coronary stent 10 having struts 12 and a central channel 16. While the examples presented in the disclosure herein are for stents, the present invention can be applied to any medical device which can be coated. Referring to FIG. 2, precursor carbon-containing material is deposited onto the surfaces of the stent struts 12 to form a precursor coating 30. The precursor carbon material may be a polymer, including polymers that are capable of forming vitreous carbon upon carbonization, such as that are three-dimensionally cross-linked and have a high molecular weight and high degree of aromaticity. For example, polymers suitable for use as precursor materials include, but are not limited to, polyfurfuryl alcohol, polyimide, polyvinyl alcohol, and cellulose. Other polymers that could be used in the present invention include varnish-based polymer films such as those described in U.S. Patent Publication No. 2005/0079200 (Rathenow et al.), which is incorporated by reference herein.

The polymer may also be polymer foams such as phenolic foams, polyolefin foams, polystyrene foams, polyurethane foams, fluoropolymer foams, or any other foam polymer which can be converted into porous carbon in a subsequent carbonizing step. In certain embodiments, foam polymers are preferred because their carbonization results in porous carbon of the type that is suitable for drug delivery.

The medical device may be coated with one or several polymer layers, partially or fully over the surface of the medical device. For a stent, the polymer coating should preferably be less than 20 μm thick. The precursor coating can be deposited by any of various methods, including spraying, dipping, sheet shrinking, plating, sputtering, chemical or physical vapor deposition, and the like, depending upon the characteristics of the coating material and the medical device substrate.

The precursor coating material is then subjected to pyrolytic decomposition under carbonization conditions to transform the coating into a carbonized layer. In the present invention, the precursor coating material is locally heated, for example, by laser irradiation using any conventional laser, including $CO_2$ and Nd:YAG lasers. The laser may heat the precursor coating material directly or indirectly by heat conduction through the body of the medical device. Whether the heating is direct or indirect can depend upon the type of laser used. For example, in a polymer coated metal stent, a $CO_2$ laser would preferably be absorbed by the polymer coating, while a Nd:YAG laser would preferably be absorbed by the metal substrate. This preferential heating capability of different lasers may be used to select or limit the area of carbonization. For example, a $CO_2$ laser can be used to heat the polymer coating while limiting heat conduction to portions of the polymer coating unexposed to the laser, such as the opposite face of the stent struts. On the other hand, an Nd:YAG laser can be used to heat the metal substrate of the stent, thereby conducting heat to portions of the polymer coating not directly exposed to the laser, such as the opposite face of the stent struts.

The laser may heat the precursor coating material to a temperature in the range of 200° C. to 2,500° C. to at least partially carbonize the precursor material. In some cases, the temperature selected is the lowest temperature that will completely carbonize the polymer materials that may be used in the present invention. In such cases, generally applicable temperatures for the carbonization step range from 200° C. to 1200° C., and in the case of certain embodiments, temperatures in the range of 250° C. to 700° C. may be used. One of skill in the art will understand that the rate, temperature, and duration of heating will influence the amount of carbonization and the porosity of the carbonized layer. Therefore, such factors can be varied to create a carbonized layer having the desired characteristics. For example, in a stent with a polymer coating of 10 μm thickness, heating at 300-500° C. for a duration of several seconds to one minute should be sufficient to completely carbonize the polymer.

The atmosphere during carbonization is essentially free of oxygen, with preferably less than 10 ppm $O_2$, and even more preferably less than 1 ppm $O_2$. The carbonization can be performed in a vacuum, in a reducing atmosphere, or in an inert atmosphere, such as an atmosphere composed of argon, neon, nitrogen, or any other inert gas or gas compounds that do not react with carbon. One of skill in the art will understand that the composition and pressure of the atmosphere will influence carbonization, and therefore, such factors can be adjusted to create a carbonized layer having the desired characteristics.

Figure 3:
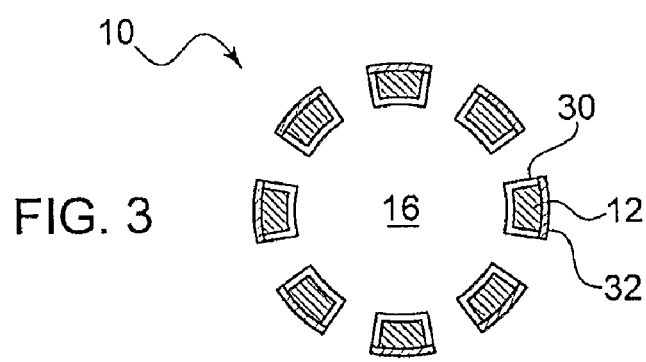
FIG. 3 is a cross-sectional view of the stent of FIG. 2 with the portion of the coating on the outer diameter of the stent having been carbonized.

In an embodiment of the present invention, laser irradiation may be used to carbonize all the precursor coating on the medical device. In other embodiments, the laser can be directed in a pattern over the medical device such that only portions of the precursor coating on the medical device are heated. For example, referring to FIG. 3, the laser may be focused so that only a portion 32 of precursor coating 30 on the outer diameter surface of stent struts 12 is carbonized. Alternatively, only the precursor coating on the inner diameter or on the side walls of the stent struts may be carbonized.

Localized carbonization may be further controlled by cooling certain areas of the medical device. Cooling can be accomplished by streaming a cooling gas or fluid, or placing a cooling object onto or in proximity of the desired area of the medical device. For example, in one embodiment, the precursor coating on the outer diameter of stent 10 may be laser irradiated, while the surface of the inner diameter is cooled by a stream of gas being passed through the inside channel 16 of stent 10. Alternatively, the precursor coating on the inner diameter of stent 10 may be laser irradiated, while a cooling gas or fluid is streamed around the outer diameter of stent 10. In another embodiment, the precursor coating on the outer diameter may be laser irradiated, while the surface of the inner diameter is cooled by direct contact with or proximity to a cooling rod inserted through the channel 16 of the stent 10. Alternatively, the precursor coating on the surface of the inner diameter may be laser irradiated, while the surface of the outer diameter is cooled by direct contact with or proximity to a hollow cooling cylinder surrounding the outer diameter of the stent 10.

With the appropriate selection of the precursor coating material and the carbonization conditions, one of skill in the art could create carbonized layers of various types and porosities. For example, using foam polymer as the precursor coating material would result in a relatively porous carbonized layer. Also, in certain embodiments of the present invention, the precursor coating material also includes additives that enlarge the diameter of the pores or increase the porosity during carbonization. Examples of suitable additives include phosphoric acid, zinc chloride, $H_2SO_4$, $K_2S$, alkali metal hydroxide, and carbonate and chlorides of $Ca^{2+}$, $Mg^{2+}$, and $Fe^{3+}$. Other suitable additives and a description of the use of such additives to influence carbonization and modify the porosity of the carbonized layer are described in U.S. Patent Publication No. 2005/0079200 (Rathenow et al.), which is incorporated by reference herein. Still more additives that influence carbonization, such as binders and fillers, are described in U.S. Pat. No. 5,820,967 (Gadkaree), which is incorporated by reference herein.

The carbonized layer can also be subjected to after-treatments such as oxidation, reduction, or incorporation of additives or fillers or other materials to further modify the porosity of the carbonized layer. Such after-treatments are described in Rathenow, which is incorporated by reference herein. For example, the hydrophilicity of the carbonized layer can be adjusted by the addition of inorganic nanoparticles into the carbonized layer. In another example, the porosity of the carbonized layer can be modified by oxidation steps or by chemical vapor deposition (CVD) processes.

The precursor carbon material and carbonization conditions may be selected to create carbonized layers having porosity suitable for promoting endothelial cell growth or migration. For example, the literature indicates that pores sizes of 200 nm to 50 um can influence endothelial cell growth.

In certain embodiments, different portions of the precursor coating can be subjected to different carbonization conditions in order to create different porosities in different portions of the resulting carbonized layer. In one embodiment, the rate, duration, and temperature of laser heating is varied in different portions of the precursor coating, resulting in different porosities in different portions of the resulting carbonized layer. In another embodiment, different portions of the precursor coating are subjected to different modifications or treatments described above, resulting in different porosities in different portions of the resulting carbonized layer. In still other embodiments, the above approaches are combined to create different porosities in different portions of the resulting carbonized layer.

For example, in a stent, a polymer foaming agent can be applied to the precursor polymer coating on the inner diameter, while another additive or no additive can be applied to the precursor polymer coating on the outer diameter of the stent. In another example, the precursor polymer coating on the inner diameter of the stent can be subjected to laser irradiation under one set of heating conditions, while the precursor polymer coating on the outer diameter of the stent is subjected to laser irradiation under a different set of heating conditions.

After carbonization, the carbonized layer on the inner diameter of the stent would have porosity characteristics different from the carbonized layer on the outer diameter. Having on the inner diameter surface one type of carbonized layer designed for endothelial cell growth, and on the outer diameter surface another type of carbonized layer designed for drug delivery, could improve the effectiveness of the stent.

Figure 4:
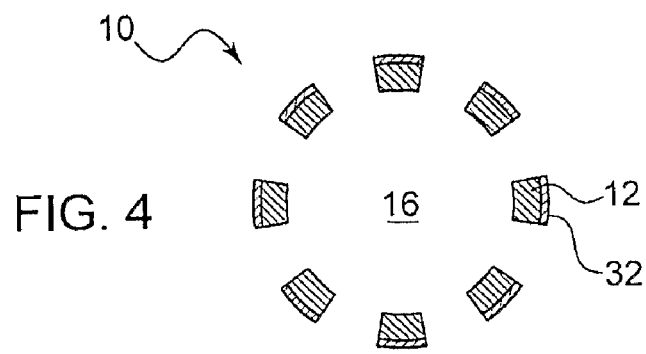
FIG. 4 is a cross-sectional view of the stent of FIG. 3 with the uncarbonized material removed by solvent washing.

Referring to FIG. 4, once the desired areas of the precursor coating are carbonized, any uncarbonized precursor coating material can be removed from the medical device by chemical or physical means. Chemical removal can be performed by washing or soaking the medical device in a solvent. The solvent may be any solvent that dissolves the uncarbonized precursor coating material, including methanol, ethanol, N-propanol, isopropanol, butoxydiglycol, butoxyethanol, butoxyisopropanol, butoxypropanol, n-butyl alcohol, t-butyl alcohol, butylene glycol, butyl octanol, diethylene glycol, dimethoxydiglycol, dimethyl ether, dipropylene glycol, ethoxydiglycol, ethoxyethanol, ethyl hexane diol, glycol, hexane diol, 1,2,6-hexane triol, hexyl alcohol, hexylene glycol, isobutoxy propanol, isopentyl diol, 3-methoxybutanol, methoxydiglycol, methoxyethanol, methoxyisopropanol, methoxymethylbutanol, methoxy PEG-10, methylal, methyl hexyl ether, methyl propane diol, neopentyl glycol, PEG-4, PEG-6, PEG-7, PEG-8, PEG-9, PEG-6-methyl ether, pentylene glycol, PPG-7, PPG-2-buteth-3, PPG-2 butyl ether, PPG-3 butyl ether, PPG-2 methyl ether, PPG-3 methyl ether, PPG-2 propyl ether, propane diol, propylene glycol, propylene glycol butyl ether, propylene glycol propyl ether, tetrahydrofuran, trimethyl hexanol, phenol, benzene, toluene, xylene; as well as water, if necessary in mixture with dispersants and mixtures of the above-named substances. In mechanical removal, physical movement of the medical device, such as ultrasonic vibration, flexing, or bending of the medical device can remove the uncarbonized precursor material.

The precursor carbon material and carbonization conditions may be selected to create carbonized layers having porosity suitable for binding or carrying therapeutic agents within the pores and releasing them in a controlled fashion. One of skill in the art can vary the porosity of the carbonized layer to control the release rate. For example, decreasing the sizes of the pores to smaller than 200 nm will slow the rate at which the therapeutic agents diffuse out of the pores. The therapeutic agent may also be combined with any pharmaceutically-acceptable excipient known in the art, such as the polymers used in drug delivery, in order to further control the release rate. Using an excipient to further control drug release may be advantageous where the pores sizes are relatively large, such as pores sizes greater than 500 nm.

Therapeutic agents may be added to the carbonized layer by any of various methods including spray coating, roll coating, absorption, adsorption, vacuum impregnation, electrophoretic transfer, and the like. The manner in which the therapeutic agents are applied will depend upon the characteristics of the carbonized layer, dimensions of the area to be coated, and the type of therapeutic agent to be applied. For example, if the carbonized layer is limited to the outer diameter, roll coating or spray coating can be used. If the carbonized area is small, inkjet methods can be used. If the sizes of the pores are too small to allow efficient penetration of therapeutic agents, vacuum impregnation or electrophoretic transfer may be suitable.

Figure 5:
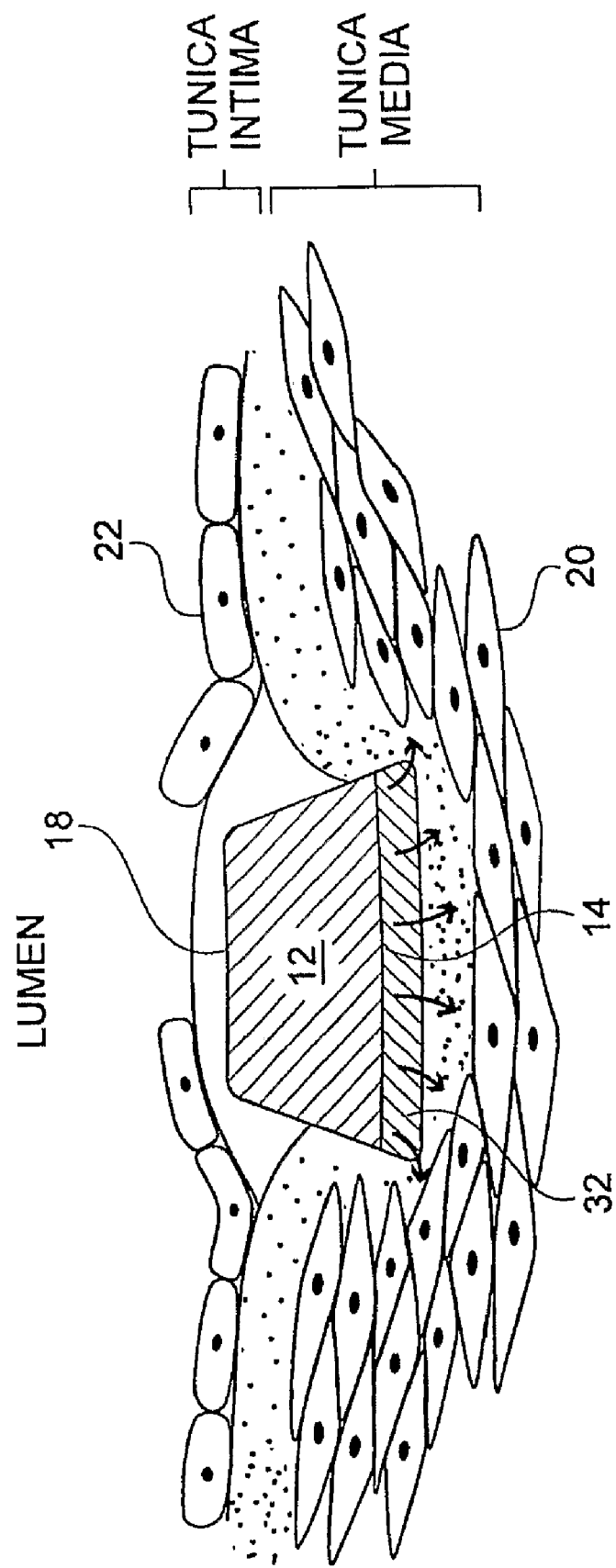
FIG. 5 is a cross-sectional view of a strut of a stent that is coated according to the method of the present invention and implanted in a blood vessel.

The method of the present invention can be used to make a medical device having a porous carbon coating limited to certain portions on the medical device, wherein the porous carbon coating carries a therapeutic agent and provides for directionally controlled release of the therapeutic agent. Thus, in a medical device having multiple surfaces or aspects, the porous carbon coating can be limited to certain surfaces or aspects in order to release the therapeutic agent with directional control. For example, FIG. 5 shows a stent strut 12 having a therapeutic agent-loaded porous carbon coating 32 limited to the outer surface 14 (facing the vessel wall) of the stent strut 12. Therapeutic agent released (indicated by the arrows) from porous carbon coating 32 would be distributed into the tunica media layer of the arterial wall, preferentially exposing the smooth muscle cells 20 to the therapeutic agent. Alternatively, the therapeutic agent-loaded porous carbon coating may be limited to the inner surface 18 (facing the lumen) of the stent strut 12 so that the therapeutic agent would be distributed into the tunica intima layer of the arterial wall, preferentially exposing the endothelial cells 22 to the therapeutic agent. A stent having this type of directionally controlled drug release would be beneficial in improving the effectiveness of stent.

The medical device of the present invention is not limited to the coronary stents in the disclosed embodiments. Non-limiting examples of other medical devices that can be coated according to the methods of the present invention include catheters, guide wires, balloons, filters (e.g., vena cava filters), stents, stent grafts, vascular grafts, intraluminal paving systems, pacemakers, electrodes, leads, defibrillators, joint and bone implants, spinal implants, vascular access ports, intra-aortic balloon pumps, heart valves, sutures, artificial hearts, neurological stimulators, cochlear implants, retinal implants, and other devices that can be used in connection with therapeutic coatings. Such medical devices are implanted or otherwise used in body structures or cavities such as the vasculature, gastrointestinal tract, abdomen, peritoneum, airways, esophagus, trachea, colon, rectum, biliary tract, urinary tract, prostate, brain, spine, lung, liver, heart, skeletal muscle, kidney, bladder, intestines, stomach, pancreas, ovary, uterus, cartilage, eye, bone, and the like.

Such medical devices may be made of any type of material in which implanted medical devices are generally made, including amorphous and/or (partially) crystalline carbon, complete carbon material, porous carbon, graphite, composite carbon materials, carbon fibres, ceramics such as e.g. zeolites, silicates, aluminium oxides, aluminosilicates, silicon carbide, silicon nitride; metal carbides, metal oxides, metal nitrides, metal carbonitrides, metal oxycarbides, metal oxynitrides and metal oxycarbonitrides of the transition metals such as titanium, zirconium, hafnium, vanadium, niobium, tantalum, chromium, molybdenum, tungsten, manganese, rhenium, iron, cobalt, nickel; metals and metal alloys, in particular the noble metals gold, silver, ruthenium, rhodium, palladium, osmium, iridium, platinum; metals and metal alloys of titanium, zircon, hafnium, vanadium, niobium, tantalum, chromium, molybdenum, tungsten, manganese, rhenium, iron, cobalt, nickel, copper; steel, in particular stainless steel, shape memory alloys such as nitinol, nickel-titanium alloys, glass, stone, glass fibres, minerals, natural or synthetic bone substance bone, imitates based on alkaline earth metal carbonates such as calcium carbonate, magnesium carbonate, strontium carbonate and any desired combinations of the above-mentioned materials.

The precursor carbon-containing material can be a polymer such as homopolymers or copolymers of aliphatic or aromatic polyolefins such as polyethylene, polypropylene, polybutene, polyisobutene, polypentene; polybutadiene; polyvinyls such as polyvinyl chloride or polyvinyl alcohol, poly(meth)acrylic acid, polyacrylocyano acrylate; polyacrylonitril, polyamide, polyester, polyurethane, polystyrene, polytetrafluoroethylene; polymers such as collagen, albumin, gelatine, hyaluronic acid, starch, celluloses such as methylcellulose, hydroxypropyl cellulose, hydroxypropyl methylcellulose, carboxymethylcellulose phthalate; waxes, paraffin waxes, Fischer-Tropsch waxes; casein, dextrans, polysaccharides, fibrinogen, poly(D,L-lactides), poly(D,L-lactide coglycolides), polyglycolides, polyhydroxybutylates, polyalkyl carbonates, polyorthoesters, polyesters, polyhydroxyvaleric acid, polydioxanones, polyethylene terephthalates, polymaleate acid, polytartronic acid, polyanhydrides, polyphosphazenes, polyamino acids; polyethylene vinyl acetate, silicones; poly(ester urethanes), poly(ether urethanes), poly (ester ureas), polyethers such as polyethylene oxide, polypropylene oxide, pluronics, polytetramethylene glycol; polyvinylpyrrolidone, poly(vinyl acetate phthalate) as well as their copolymers, mixtures and combinations of these homopolymers or copolymers.

The therapeutic agent in a coating of a medical device of the present invention may be any pharmaceutically acceptable agent such as a non-genetic therapeutic agent, a biomolecule, a small molecule, or cells.

Exemplary non-genetic therapeutic agents include antithrombogenic agents such heparin, heparin derivatives, prostaglandin (including micellar prostaglandin E1), urokinase, and PPack (dextrophenylalanine proline arginine chloromethylketone); anti-proliferative agents such as enoxaparin, angiopeptin, sirolimus (rapamycin), tacrolimus, everolimus, zotarolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as nonsteroidal anti-inflammatory agents and chelating agents such as ethylenediaminetetraacetic acid, O,O'-bis (2-aminoethyl) ethyleneglycol-N,N,N',N'-tetraacetic acid and mixtures thereof; antibiotics such as gentamycin, rifampin, minocyclin, and ciprofloxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms; inhibitors of heat shock proteins such as geldanamycin; angiotensin converting enzyme (ACE) inhibitors; beta-blockers; βAR kinase (βARK) inhibitors; phospholamban inhibitors; protein-bound particle drugs such as ABRAXANE™; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include SERCA-2 protein, monocyte chemoattractant proteins (MCP-1) and bone morphogenic proteins ("BMPs"), such as, for example, BMP-2, BMP-3, BMP-4, BMP-5, BMP-6 (VGR-1), BMP-7 (OP-1), BMP-8, BMP-9, BMP-10, BMP-11, BMP-12, BMP-13, BMP-14, BMP-15. Preferred BMPs are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them. Non-limiting examples of genes include survival genes that protect against cell death, such as anti-apoptotic Bcl-2 family factors and Akt kinase; SERCA-2 gene; and combinations thereof. Non-limiting examples of angiogenic factors include acidic and basic fibroblast growth factors, vascular endothelial growth factor, epidermal growth factor, transforming growth factors α and β, platelet-derived endothelial growth factor, platelet-derived growth factor, tumor necrosis factor α, hepatocyte growth factor, and insulin-like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative (Lin$^-$) cells including Lin$^-$CD34$^-$, Lin$^-$CD34$^+$, Lin$^-$cKit$^+$, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts +5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

Any of the therapeutic agents may be combined to the extent such combination is biologically compatible.

The foregoing description and examples have been set forth merely to illustrate the invention and are not intended to be limiting. Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

What is claimed is:

1. A method of coating a medical device, comprising the steps of:
   (a) providing a medical device at least partially coated with a precursor carbon material, wherein the medical device has a first portion and a second portion; and
   (b) heating the precursor carbon material on at least the first portion of the medical device with a laser, wherein the heating causes carbonization of the precursor carbon material to form a carbonized layer;
   wherein the precursor carbon material on the second portion of the medical device is not carbonized; and
   (c) removing any uncarbonized precursor material from the medical device.

2. The method of claim 1, wherein the medical device is a stent.

3. The method of claim 2, wherein the first portion is the outer diameter surface of the stent.

4. The method of claim 2, wherein the first portion is the inner diameter surface of the stent.

5. The method of claim 2, wherein the first portion is the side walls of the stent.

6. The method of claim 1, wherein the precursor carbon material is a polymer.

7. The method of claim 6, wherein the polymer is a foam polymer.

8. The method of claim 1, wherein the precursor carbon material on the first portion and a third portion of the medical device are heated with a laser, and wherein the porosity of the carbonized layer in the first portion is different from the porosity of the carbonized layer in the third portion.

9. The method of claim 8, wherein the differing porosities are created by the use of additives in the precursor carbon material.

10. The method of claim 8, wherein the differing porosities are created by after-treatments to the carbonized layer.

11. The method of claim 8, wherein the differing porosities are created by heating the precursor carbon material on the first portion under one set of heating conditions, and heating the precursor carbon material on the third portion under a different set of heating conditions.

12. The method of claim 1, further comprising cooling the second portion of the medical device before, during, or after heating the precursor carbon material on the first portion.

13. The method of claim 3, further comprising cooling the second portion of the stent before, during, or after heating the precursor carbon material on the first portion, and wherein cooling the second portion comprises inserting a cooling rod through a channel of the stent.

14. The method of claim 3, further comprising cooling the second portion of the stent before, during, or after heating the precursor carbon material on the first portion, and wherein cooling of the second portion comprises streaming a cooling fluid through a channel of the stent.

15. The method of claim 4, further comprising cooling the second portion of the stent before, during, or after heating the precursor carbon material on the first portion, and wherein cooling of the second portion comprises surrounding the stent with a cooling element.

16. The method of claim 4, further comprising cooling the second portion of the stent before, during, or after heating the precursor carbon material on the first portion, and wherein cooling of the second portion comprises streaming a cooling fluid around the stent.

17. The method of claim 1, wherein removing any uncarbonized precursor material comprises washing with a solvent.

18. The method of claim 1, further comprising incorporating a therapeutic agent into the carbonized layer.

19. The method of claim 1, wherein providing a medical device coated with a precursor carbon material comprises applying a precursor carbon material onto the medical device.

* * * * *